United States Patent [19]

Vanderpool

[11] Patent Number: 4,698,427

[45] Date of Patent: Oct. 6, 1987

[54] CATALYTIC METHOD FOR THE CONJOINT MANUFACTURE OF N-AMINOETHYLPIPERAZINE AND TETRAETHYLENEPENTAMINE

[75] Inventor: Steven H. Vanderpool, New Braunfels, Tex.

[73] Assignee: Texaco Inc., White Plains, N.Y.

[21] Appl. No.: 871,953

[22] Filed: Jun. 9, 1986

[51] Int. Cl.[4] .................... C07D 241/04; C07C 85/06
[52] U.S. Cl. .................... 544/404; 564/479; 564/485; 564/509; 564/512
[58] Field of Search ............... 544/404; 564/479, 485, 564/509, 512

[56] References Cited

U.S. PATENT DOCUMENTS

| | | | |
|---|---|---|---|
| 3,037,025 | 5/1962 | Godfrey | 544/404 |
| 3,159,633 | 12/1964 | Laufdon et al. | 544/404 |
| 3,167,551 | 1/1965 | Weiport | 544/404 |
| 3,249,613 | 5/1966 | Burns et al. | 544/404 |
| 3,697,524 | 10/1972 | Tomolia et al. | 544/404 |
| 3,732,311 | 5/1973 | Baron | 544/404 |
| 4,036,881 | 7/1977 | Brennan et al. | 564/512 |
| 4,105,657 | 8/1978 | Dockner et al. | 544/404 |
| 4,316,840 | 2/1982 | Ford et al. | 564/512 |
| 4,588,842 | 5/1986 | Vanderpool | 564/512 |
| 4,647,664 | 3/1987 | Vanderpool | 564/479 |

FOREIGN PATENT DOCUMENTS 2316358 10/1974 Fed. Rep. of Germany ...... 544/404

OTHER PUBLICATIONS

Vanderpool et al., CA 101-194142v.

*Primary Examiner*—Donald G. Daus
*Assistant Examiner*—Cecilia Shen
*Attorney, Agent, or Firm*—Jack H. Park; Kenneth R. Priem

[57] ABSTRACT

Ethylenediamine and diethanolamine and/or hydroxyethyldiethylenetriamine can be converted to N-aminoethylpiperazine and tetraethylenepenetamine when using a catalyst composed of titania to which from about 0.5 to about 7 wt. % of phosphorus has been thermally chemically bonded in the form of phosphate linkages.

6 Claims, No Drawings

CATALYTIC METHOD FOR THE CONJOINT MANUFACTURE OF N-AMINOETHYLPIPERAZINE AND TETRAETHYLENEPENTAMINE

BACKGROUND OF THE INVENTION

1. Field of the Invention

This invention relates to a catalytic method for the conjoint preparation of N-aminoethylpiperazine and tetraethylenepentamine. More particularly, this invention relates to a catalytic method for the conjoint manufacture of N-aminoethylpiperazine and tetraethylenepentamine from ethylenediamine and diethanolamine. Still more particularly, this invention is directed to the use of a titania catalyst to which a minor amount of phosphorus has been thermally chemically bonded at the surface thereof in the form of phosphate linkages for the conjoint manufacture of N-aminoethylpiperazine and tetraethylenepentamine by passing ethylenediamine and diethanolamine over a catalyst composed of titania to which a minor amount of phosphorus (0.5 to 7 wt. %) has been thermally chemically bonded in the form of phosphate linkages.

2. Prior Art

The catalysts used in the practice of the process of the present invention are disclosed in Vanderpool European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

Ford U.S. Pat. No. 4,316,841 discloses a process for reforming polyalkylene polyamines, preferably to non-cyclic polyalkylene polyamines, using as the catalyst a phosphate of a Group IA or Group IIA, preferably boron phosphate. European patent application No. 151,232 is directed to a process for converting piperazine to ethylenediamine and N-aminoethylpiperazine by reductively aminating piperazine a reductive amination catalyst such as a metal or oxide of copper, nickel, cobalt, palladium, rhodium, etc.

The preparation of N-aminoethylpiperazine by the hydrogenation of nitrileacetonitrile using a hydrogenation catalyst, such as a nickel, copper, iron, palladium, cobalt, chromium, rhodium, molybdenum or titanium catalyst is disclosed in Yeakey U.S. Pat. No. 3,733,525. McConnel U.S. Pat. No. 4,324,917 is directed to the use of a phosphorus-containing cation exchange resin to promote the reaction of an alkanolamine with an alkyleneamine to provide predominantly non-cyclic polyalkylene polyamine reaction products. In Brennan et al. U.S. Pat. No. 4,049,657 a process is disclosed for selectively preparing N-aminoethylpiperazine by cycling a primary or secondary amino alkanol in the presence of a catalytically effective amount of a phosphorus compound such as an acidic metal phosphate, a compound of phosphoric or phosphorous acid, an alkyl or aryl phosphate or phosphite, etc. European patent application No. 0,138,050 discloses a process for preparing polyalkylene polyamines by reacting an alkanolamine with ammonia or a primary or secondary amine in the presence of a Group IIIB metal acid phosphate, such as a phosphate, monohydrogen phosphate or dihydrogen phosphate (e.g., a lanthanium, praseodymium or neodymium phosphate).

SUMMARY OF INVENTION

It has been surprisingly discovered in accordance with the present invention that ethylenediamine (EDA) and diethanolamine (DEA) may be conjointly converted to N-aminoethylpiperazine (AEP) and tetraethylenepentamine (TEPA) by using a catalyst composed of titania to which from about 0.5 to about 7 wt. % of phosphorus has been thermally chemically bonded in the form of phosphate linkages.

DETAILED DESCRIPTION OF THE EMBODIMENT

Feedstocks

The feedstocks to be used in accordance with the present invention are ethylenediamine and diethanolamine. Hydroxyethyldiethylenetriamine (HEDETA), a by-product of the reaction may be recycled as a feed component or may be separately reacted with the ethylenediamine.

In general, about 1 to 5 mols of diethanolamine should be used per mol of ethylenediamine. Since ethylenediamine is soluble in diethanolamine, it is convenient to use a diethanolamine solution of ethylenediamine containing about 10 to about 50 wt. % of ethylenediamine. As indicated, HEDETA may be substituted for all or a part of the diethanolamine on a mol equivalent basis.

Catalysts

The process of the present invention may be conducted on a batch basis using powdered catalyst or on a continuous basis using pelleted catalyst.

The catalyst compositions of the present invention are prepared by depositing a phosphorus compound on titania, as described in greater detail in copending Vanderpool application Ser. No. 06/564,153 filed Dec. 22, 1983, and entitled "Catalytic Preparation of Linear Polyethylenepolyamines" and in Vanderpool European patent application Ser. No. 83,387,520.3 published Aug. 28, 1984. Pellets of titania may be prepared by extrusion or by compaction in conventional pelleting apparatus using a pelleting aid such as graphite. It is also within the scope of the present invention to deposit the phosphorus compound on powdered titania.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diammonium phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

As a matter of convenience, the normal practice is to use only one chemical as a phosphorus source (e.g., aqueous phosphoric acid). However, mixtures of two or more such reagents may be used if desired.

The catalyst composition can be prepared by impregnating a preformed pellet. A suitable procedure to be used is to heat the water soluble or liquid phosphorus compound at a temperature of about 100° to about 150° C. and to then add titania pellets in an amount about equal to the volume of the heated liquid. This treatment should be continued from about 0.5 to about 5 hours. At the end of that time, the resulting mixture of pellets and liquid is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated pellet is not present as elemental phosphorus, but rather as phosphorus that is chemically bound, probably as an oxide, to the titania support. This is demonstrated by the fact that repeated washing will not remove all of the phosphorus. However, the exact nature of the bonding is not completely understood.

The amount of phosphorus that is bonded to the support is a function of heating and other conditions used in the treating step and is also a function of the chemical identity of the phosphorus compound that is used as a source of phosphorus. Under the treating conditions exemplified above, at least about 0.5 wt. % of phosphorus is caused to bond (i.e., permanently adhere) to the pellets. There is an upper limit to the amount of phosphorus that bonds to the support. This upper limit is, as indicated, a function of both the treating conditions and the chemical used as a source of the phosphorus. Normally, the maximum amount of phosphorus that can be caused to bond to the pellets is about 7 wt. %.

When the pellets are impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania. For example, the pellets can be treated with the phosphorus compound at ambient temperatures or at more modest elevated temperatures of less than about 100° C.

Alternatively, the titania can be treated with the phosphorus-containing compound in powdered form and the powder can be used, as such, or can be pelleted. If the treatment is conducted at a temperature of about 100° C. or more, thermal activation will normally have been obtained and it will not be absolutely necessary to perform a calcining operation prior to use. If lower treating temperatures are used, calcining prior to use is normally a desired operation. The calcining operation can be conducted prior to or subsequent to the pelleting step. Any appropriate pelleting procedure of the type known to those skilled in the art may be used. For example, the treated powdered titania or zirconia can be mixed with graphite and/or other binders and compacted or extruded under conventional conditions.

In any event, in-situ calcining will occur when the catalyst compositions are used to catalyze the reaction of ethylenediamine with diethanolamine and/or HEDETA to provide AEP and TEPA, as is hereinafter more fully set forth.

Reaction Conditions

The reaction of the present invention is conducted utilizing a feedstock of the present invention comprising diethanolamine and/or HEDETA dissolved in ethylenediamine so as to form about a 10 to about 50 wt. % solution of diethanolamine and/or HEDETA in ethylenediamine, such as a 10 to 20 wt. % solution, which is brought into contact with a catalyst in a batch reactor or in a continuous reactor. This will provide the desired mol ratio of reactants.

The reaction is suitably conducted at a temperature of about 250°–400° C. and, more preferably, at a temperature of about 300° to about 350° C.

The reaction is also preferably conducted under pressure up to about 3000 psig although atmospheric pressure may be utilized if desired. Preferably, the reaction is conducted at a pressure of about 1000 to about 2000 psig.

When the reaction is conducted on a batch basis, the reaction time may suitably vary from about 1 to about 24 hours. When the reaction is conducted on a continuous basis, the feedstock may suitably be passed over a bed of pelleted catalyst at a liquid hourly space velocity (lhsv) of about 0.2 to about 5 volumes of the aqueous solution of the amine feedstock per volume of catalyst per hour. More preferably, the lhsv will be from about 0.5 to about 2.

It is not necessary to use either ammonia or hydrogen as feed components in the practice of the process of the present invention.

EXAMPLES

Equipment and Procedures

In all cases, these evaluations were performed in a 25 cc reactor constructed of $\frac{3}{4}$ inch stainless steel tubing connected to $\frac{1}{8}$ inch feed and effluent lines with swagelok fittings. The reactor tube was situated inside of a 3×3 inch aluminum block which was heated electrically with four 1,000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly. The reactor effluent was collected in a glass jug and sampled after the system had lined-out at the proscribed temperature for at least 2.5 hours.

The catalyst that was used was prepared from titania and concentrated phosphoric acid. It had about 2 wt. % of phosphorus thermally chemically bonded thereto and was prepared by dipping preformed titania pellets into a 30% polyphosphoric acid solution, followed by decanting and calcining at 450° C.

Analysis of the reactor effluent was achieved using an OV-17 column in a Hewlett-Packard 5710A gas chromatograph. Analysis was on a water-free and feed-free basis. Since the conversion of HEP and BisHEP were nearly quantitative, the selectivities were close to calculated yields.

EXAMPLE 1

These runs were at 1400 psig. using the equipment and procedures described above. At 315° C., DEA conversion was 100%. Product selectivities were:

| | |
|---|---|
| Tetraethylenepentamine (TEPA) | 43% |
| N—aminoethyl piperazine (AEP) | 25% |
| Hydroxyethyldiethylene triamine (HEDETA) | 8% |
| Diethylenetriamine (DETA) | 15% |

| | -continued | |
|---|---|---|
| Triethylene tetramine (TETA) | | 3% |

The feed consisted of 10 wt. % DEA in EDA. HEDETA was formed as the primary intermediate which was converted to either AEP by intramolecular cyclization or TEPA by reaction with another mole of EDA. It is surprising that the bimolecular reaction effectively competes with and, indeed, reacts faster than the intramolecular reaction. The selectivities shown above are GC area % on a feed-free basis.

EXAMPLE 2

In this experiment, using the equipment and procedures described above, the feed consisted of 33 wt. % DEA in EDA. Again DEA conversion was 100% at 315° C. Product selectivities were:

| | |
|---|---|
| TEPA | 21% |
| AEP | 31% |
| HEDETA | 28% |
| DETA | 5% |
| TETA - peak lost under HEDETA | |

The major impact of increased concentration of DEA in the feed appears to be loss of TEPA selectivity and increased HEDETA yields. HEDETA is recyclable.

The data above indicates that the relative yields of AEP & TEPA can be adjusted by manipulating the feed ratios.

EXAMPLES 3-9

These runs were performed at 1100 to 1300 psig. using the equipment and procedures described above. Using a feed consisting of 2230 g EDA and 1190 g HEDETA, the results shown in Table I were obtained. The selectivities are calculated from GC analysis of the crude reactor effluent on a feed-free basis.

TABLE I

| Ex | Temp (°C.) | HEDETA Conv. | Selectivity | | |
|---|---|---|---|---|---|
| | | | DETA | AEP | TEPA |
| 3 | 301 | 79% | 5% | 35% | 44% |

TABLE I-continued

| Ex | Temp (°C.) | HEDETA Conv. | Selectivity | | |
|---|---|---|---|---|---|
| | | | DETA | AEP | TEPA |
| 4 | 305 | 84% | 10% | 32% | 41% |
| 5 | 310 | 89% | 12% | 31% | 38% |
| 6 | 316 | 92% | 18% | 28% | 31% |
| 7 | 320 | 93% | 19% | 27% | 30% |
| 8 | 325 | 94% | 18% | 27% | 29% |
| 9 | 330 | 93% | 20% | 25% | 23% |

This data should be compared to that presented where DEA is reacted with EDA to give the same products. This is due to the in-situ formation of HEDETA in that reaction.

The foregoing examples are given by way of illustration only and are not intended as limitations on the scope of this invention, as defined by the appended claims.

What is claimed is:

1. A method for the conjoint manufacture of N-aminoethylpiperazine and tetraethylenepentamine which comprises bringing a solution of diethanolamine and/or hydroxyethyldiethylenetriamine in ethylenediamine containing about 10 to about 50 wt. % of diethanolamine and/or hydroxyethyldiethylenetriamine with a cyclization catalyst at a temperature of about 250°–400° C. for a period of time sufficient to convert at least a portion of said feed component to N-aminoethylpiperazine and tetraethylenepentamine, said catalyst composition comprising titania having from about 0.5 to about 7 wt. % of phosphorus thermally chemically bonded to the surface thereof in the form of phosphate bonds.

2. A method as in claim 1 wherein the reaction is conducted at a temperature of about 250° to about 400° C. and a pressure of about 0 to about 3000 psig.

3. A method as in claim 2 wherein the reaction is conducted at a temperature of about 300° to about 350° C. and a pressure of about 1000 to about 2000 psig.

4. A method as in claim 3 wherein the feedstock components are ethylenediamine and diethanolamine.

5. A method as in claim 3 wherein the feedstock components are ethylenediamine and a mixture of diethanolamine with hydroxyethyldiethylenetriamne.

6. A method as in claim 3 wherein the feedstock components are ethylenediamine and hydroxyethyldiethylenetriamine.

* * * * *